United States Patent [19]
Liu et al.

[11] Patent Number: 5,262,166
[45] Date of Patent: Nov. 16, 1993

[54] RESORBABLE BIOACTIVE PHOSPHATE CONTAINING CEMENTS

[76] Inventors: Sung-Tsuen Liu, 29 Landing, Laguna Niguel, Calif. 92677; Harvey H. Chung, 43 Via Costa Verde, Rancho Palos Verdes, Calif. 90274

[21] Appl. No.: 687,586

[22] Filed: Apr. 17, 1991

[51] Int. Cl.$^5$ .................. A61F 2/02; A61F 2/28; C09K 3/10
[52] U.S. Cl. .................... 424/423; 623/16; 106/35; 106/690; 106/691
[58] Field of Search .................. 424/423; 623/16; 106/35, 690, 691

[56] References Cited

FOREIGN PATENT DOCUMENTS 9008520 8/1990 PCT Int'l Appl. .................. 623/16

Primary Examiner—Thurman K. Page
Assistant Examiner—C. Azpuru
Attorney, Agent, or Firm—Drucker & Sommers

[57] ABSTRACT

A surgical cement of high biocompatibility, useful in orthopedic, maxillofacial and dental applications, comprising a calcium alkali phosphate cement with relatively high surface pH of about 7 or higher, and having a wide variety of chemical compositions, permitting flexibility in controlling the bioresorption rate by changing the chemical composition of the cementing powder.

17 Claims, No Drawings

RESORBABLE BIOACTIVE PHOSPHATE CONTAINING CEMENTS

BACKGROUND OF THE INVENTION

1. Field of the Invention

This invention relates to a surgical cement, also known as bone cement or bioresorbable implantation material, and its process of formation. The cements of this invention are formed from calcium alkali phosphate ceramics and acidic citrate setting reagents, which when combined with an aqueous solution form a moldable paste having high biocompatibility. The paste is easy to manipulate and reaches neutral pH or higher shortly after hardening. The resulting cements are useful in orthopedic and maxillofacial surgeries and in dental applications.

2. Description of the Prior Art

In the last two decades, many artificial hard tissue implant materials have been made. Since the major inorganic component of human hard tissue (e.g. bone, teeth) is a calcium phosphate compound, which is biological apatite, hydroxyapatite and other calcium phosphate ceramics were logically selected for hard tissue implant materials.

Most of the previous calcium phosphate cements developed used hydroxyapatite or tricalcium phosphate as the cementing ceramic and phosphoric acid, bifunctional organic acids or other polyfunctional organic acids as setting reagents. These cements are normally very acidic in nature and take a very long time to reach neutral pH. After implantation, these cements may cause irritation and inflammatory reactions.

Biocompatibility has been the limiting factor in successful applications of implant materials. The most successful artificial implant materials to achieve the excellent biocompatibility have been hydroxyapatite, bioglass[1], and other calcium phosphate ceramics. Hydroxyapatite and $\beta$-tricalcium phosphate ceramics and calcium phosphate containing glass have been extensively studied. Clinical studies confirmed that most of the calcium phosphate ceramics such as hydroxyapatite, tricalcium phosphate, tetracalcium phosphate and dicalcium phosphate have excellent biocompatibility and are well accepted by both hard tissue and soft tissue. The experimental results also indicated that dense hydroxyapatite is non-bioresorbable while other porous calcium phosphate ceramics are bioresorbable.

[1] A bioactive glass material whose major components are CaO, SiO$_2$ and P$_2$O$_5$. Minor components may be Na$_2$O, MgO, Al$_2$O$_3$, B$_2$O$_3$ and CaF$_2$. A bioactive glass can form a surface layer of hydroxyapatite when soaked in the aqueous environment.

The surgeon is most interested in implant materials that can be shaped and harden in situ, but such bioceramic preparations are not yet available. Most of the calcium phosphate ceramics for medical applications are prepared either in granule form or block form. The granule form has poor manipulation characteristics while the block form is very brittle and difficult to shape. In order to solve the above problems, many attempts have been made to prepare binder systems for bioceramics. Plaster of Paris, collagen, polylactate, polyacrylate, calcium phosphate grout and hydroxyapatite cement have been used.

Ideally, a useful binder system for bioceramics should have good biocompatibility, (including a near neutral pH), a suitable bioresorption rate, be moldable at surgical sites, and have good setting characteristics. The acidity of the setting cement is dependent on the type of calcium phosphate salt used, the acidity of the setting reagent, and the reaction rate. Typical cements are formed from dissolution and recrystallization of salts with Ca/P mole ratio > 1 after combination with acidic reagents.

When the calcium phosphate salt reacts with the acid setting reagent to form a cement, the calcium phosphate dissolves and new calcium compounds are formed during the setting stage. The extent of the reaction, the setting time and setting characteristics are sensitive to the nature of calcium phosphate powder, the pH and the type of setting reagents. Even when excess calcium phosphate powder is used to form a paste with highly soluble acidic setting reagent, the setting cement will nevertheless contain some unreacted acid setting reagent trapped in the cement. The result is a low surface pH of the setting cement. If the calcium phosphate cementing powder is near neutral and has a very slow dissolution rate, the surface pH will stay low for a long time. This low pH cement is undesirable since it may cause irritation and inflammatory reactions. Additionally setting times of this cement are difficult to control and it has poor manipulation characteristics.

Most binders have disadvantages. Plaster of Paris has a reasonable setting characteristics but the resorption rate is too fast. Collagen-hydroxyapatite composites and polylactatehydroxyapatite can serve as a useful delivery system for hydroxyapatite or other calcium phosphate granular ceramics, but these composite materials must be premolded; they cannot be molded at the surgical site.

Calcium phosphate grout does not set well in the in situ aqueous environment. For example, a recently reported calcium phosphate cement combined with bifunctional acids as setting reagents (U.S. Pat. No. 4,668,295) was very acidic, disintegrated very fast in the in situ aqueous environment, and lacked good setting characteristics. Pure hydroxyapatite cement prepared by reacting tetracalcium phosphate and other calcium phosphates is not resorbable and does not have good setting characteristics (U.S. Pat. Nos. 4,518,430 and 4,612,053).

Oonishi[2] reported a bioactive $\alpha$-tricalcium phosphate cement. This calcium phosphate cement has a reasonable setting time and strong mechanical strength, but is very acidic. More recently, a bioglass cement containing calcium phosphate using phosphoric acid or calcium hydroxide as the setting reagent has been reported.[3] The bioglass cement with phosphoric acid has low pH. No setting characteristic of this bioglass cement has been reported.

[2] H. Oonishi, et al, "Studies on Development of $\alpha$-TCP Bioactive Bone Cement" Posted Paper, Engineering Foundation Conferences, Bioceramics, Santa Barbara, Calif. 1986.

[3] W. S. Chen, Y. Chen, J. P. Rausch, E. A. Monroe, "Phosphate Glass Bone Graft", page 241, The 15th Annual Meeting of the Society for Biomaterials, Apr. 28-May 2, 1989, Lake Buena Vista, Fla.

SUMMARY OF THE INVENTION

This invention relates to surgical cements formed by combining calcium alkali phosphate ceramics with acidic citrate setting reagents which shortly after setting have near neutral surface pH (pH 7) and are highly biocompatible, moldable, and resorbable. Since the material of this invention may be mixed to vary the reaction rates, greater flexibility of use may be expected because the medical technician could apply this invention in paste form in situ or premold the implant.

The present invention uses a highly alkaline and rapidly dissolving calcium alkali phosphate ceramic, such as calcium sodium phosphate or calcium potassium phosphate ceramics which result in the increased surface pH of the surgical cement and hence the greater biocompatibility.

Additionally, the present invention provides increased bioresorption and improved manipulation characteristics. This invention permits manipulation of the cementitious paste at the surgical site for hard tissue replacement within a reasonable setting time. It can also be prepared in premolded shapes.

Resorption rates can be varied by predetermined mixtures of biocompatible filler compounds added to the cementing powders. These cements are only slightly acidic after mixing into a paste. After setting in the liquid environment, the surface pH of the cements raises rapidly to near 7 or higher.

In summary, the advantages of these cements are relatively high surface pH, good biocompatibility, bioresorbability, reasonable setting time and good manipulation characteristics. Consequently, these cements have greater usefulness as implants for hard tissue replacement materials over prior art. They can be used for bone graft, bone fracture fixation, bone defect fillers, maxillofacial surgery, spinal fusion, bone cements, dental cements and drug delivery systems. They can also be used as a binder system for the granule form of calcium phosphate ceramics.

DETAILED DESCRIPTION OF THE PREFERRED EMBODIMENTS

Among the pure calcium phosphate salts, only tetracalcium phosphate is alkaline in nature. In a preparation of calcined phosphate fertilizer, Ando[4] and Ando and Matsuno[5] reported the formation of mixed ceramics. This mixed ceramic is a crystalline solid solution containing tricalcium phosphate, $Ca_5Na_2(PO_4)_4$ and rhenantite ($\alpha$ and $\beta$ form of $CaNaPO_4$). In general, these calcium sodium phosphate ceramics are alkaline in nature, and have relatively high solubility. Similarly, the calcium potassium phosphate ceramics are also alkaline and have high dissolution rates. The present invention uses these calcium alkali containing phosphate ceramics for the cementing powder. Because of the alkaline nature and high dissolution rates, these ceramics are able to react with acidic citrate compounds yielding cements with relatively short setting times ranging from several minutes to about a half an hour, and having high surface pH.

[4] J. Ando, "Phase Diagrams of $Ca_3(PO_4)_2$-$Mg_3(PO_4)_2$ and $Ca_3(PO_4)_2$-$CaNaPO_4$ Systems". Bull. Chem. Soc., Japan, 31, 201 (1958).
[5] J. Ando and S. Matsuno, "$Ca_3(PO_4)_2$-$CaNaPO_4$ System". Bull. Chem. Soc., Japan, 41, 342 (1968).

The setting reagents used in this invention are acidic citrate compounds, including citric acid, dihydrogen citrate salts or monohydrogen citrate salts. In the present cement system, the weight ratio of cementing powder to setting reagent varies from 1:2:1 to 10:1. When the ratio is as high as 10, the final set cement contains reaction products and high amounts of bioresorbable unreacted calcium alkali phosphate.

A further increase of the surface pH of the setting cement may be achieved by using hydrogen citrate salts or citric acid with alkaline reagents instead of using pure citric acid as the setting reagent. Among the suitable hydrogen citrate salts are: sodium dihydrogen citrate, disodium hydrogen citrate, ammonium dihydrogen citrate, diammonium hydrogen citrate, potassium dihydrogen citrate and dipotassium hydrogen citrate.

The pH may also be raised by using citric acid with alkaline reagents. Suitable akaline reagents include NaOH, KOH, $NH_4OH$, sodium citrate, potassium citrate, ammonium citrate, sodium phosphate, disodium hydrogen phosphate, potassium phosphate, and dipotassium hydrogen phosphate. While the pH of concentrated pure citric acid is normally at 2, the pH modified setting reagent should provide an initial solution pH which is much higher than the pure citric acid, reaching a pH of 3 to 5. Therefore, after setting, the surface pH of the setting cement will initially be near 5 and quickly reach 7 or higher upon hardening.

The surgical cement of this invention relates to a flexible composition by changing the $CaO:Na_2O$ or $CaO:K_2O$ mole ratios in the calcium alkali phosphate ceramics. The dissolution rate as well as the bioresorption rate of the cement changes accordingly. The overall chemical composition of these ceramics can be changed from $2.9\ CaO.0.1\ Na_2O.P_2O_5$ to $0.8\ CaO.2.2\ Na_2O.P_2O_5$. The calcium potassium phosphate ceramics can be varied in composition in the same manner. While these mixed ceramics cover a wide variety of chemical compositions and a wide range of dissolution rates, in general, the dissolution rates increase by increasing the alkali element content. As a result, the technician can achieve greater bioresorption rate control with the mixed ceramics than with the pure single component calcium phosphate cements.

Further control of the bioresorption rat in this invention is achieved by incorporating a biocompatible filler material in the form of fine powder or granule, having a particle size ranging from a few microns to 20 mesh. Filler material must be biocompatible without significantly effecting the integrity and setting behavior of the cement. Fillers useful for this purpose include tetracalcium phosphate, tricalcium phosphate, calcium phosphate apatite, dicalcium phosphate, calcium carbonate, calcium sulfate dihydrate, calcium sulfate hemihydrate, calcium sulfate anhydrous, calcium fluoride, calcium oxide, calcium hydroxide, calcium citrate, magnesium hydroxide, magnesium oxide, collagen and other sparingly calcium organic salts. The weight ratio of filler to calcium alkali phosphate cementing powder can be up to 5:1.

In the present invention the cementing powder was premixed with filler material to form a homogeneous mixed powder. The setting reaction can be initiated either by dissolving the setting reagent and pH adjustment reagents in water or saline water to form an aqueous setting solution and adding it to the premixed powder, or premixing the solid setting reagents with the cementing powder and using sterilized pure water or saline water as the setting aqueous solution.

The cements of the present invention may be used as implant materials for: (1) bone grafts as filler or replacement of bone that has been removed surgically or due to traumatically; (2) ridge augmentations; (3) jaw repairs; (4) cranial and maxillofacial surgeries; (5) luting cement in dentistry and orthopedic surgery; (6) spinal fusions; (7) endodontic applications; (8) root cements; (9) replacing or promoting regeneration of bone mineral lost due to periodontal disease; and (10) drug release systems. Antibiotics (up to 20% of cement) by weight and bone growth proteins (up to 10% of cement by weight) are the preferred drugs to be released by the cement of this invention.

The strength as well as the setting time of the present cements are directly dependent on the nature and particle size of the calcium alkali phosphate ceramics, the nature of the filler powder, the type and amount of the setting reagent, and the solid powder to liquid ratio. In general, with other factors constant, the strength increases as the particle size of the powder decreases. The setting time increases as the cementing powder to setting reagent weight ratio decreases.

The cement can be molded to any shape before use. For example, when used as a drug delivery system, the required amount of the drug is mixed with the cementing powder and setting reagent to form paste first. After setting, the hardened cement may be broken into a suitably sized granules. This drug containing cement is then dried and stored before use. For more convenient applications at the surgical site, the cement can then be prepared as a paste first. The paste can be introduced into the bone defects or implantation site before it becomes hardened.

This invention may be prepared as a kit, comprising a selected cementing powder and setting reagent which when admixed with aqueous solution will form a paste. This paste will harden in a short time and will reach a pH near 7 or higher.

EXAMPLE 1

Pure $CaNaPO_4$ (calcium sodium phosphate) ceramic was prepared by solid state reaction at high temperature. Stoichiometric amounts of $CaHPO_4$ and $Na_2CO_3$ corresponding to the formation of $CaNaPO_4$ were homogeneously mixed. The mixed powder was then sintered at high temperature to form $CaNaPO_4$ ceramic. The ceramic was then ground to fine powder. 2 g of the $CaNaPO_4$ powder was mixed with 0.8 g of solid citric acid. A few drops of pure water was then added to form a sticky paste. After mixing, the paste set within several minutes. Shortly after setting, the surface pH of the set cement was tested with pH indicator paper. Initially, the surface pH was near 5; it reached 7 or higher in less than a half hour. The hardened cement aged in pure water did not show any sign of disintegration.

EXAMPLE 2

2 g of $CaNaPO_4$ fine ceramic powder prepared from example 1 was premixed with 0.3 g of citric acid and 0.3 g of trisodium citrate. The premixed powder was then mixed with few drops of pure water to form a homogeneous paste. This paste set in a few minutes. After setting, the initial surface pH was near 6 and reached 7 or higher in less than half hour.

EXAMPLE 3

$CaNaPO_4$ mixed ceramics having an overall chemical composition of $2.7\ CaO.0.3\ Na_2O.P_2O_5$ were prepared by solid state reaction at high temperatures. Required amounts of $CaHPO_4$, $Na_2CO_3$ and $CaCO_3$ were mixed homogeneously and sintered. After sintering, the prepared mixed ceramics were ground to fine powder, and 2 g of the prepared ceramics powder was mixed with 0.6 g of anhydrous citric acid. This mixed powder was then mixed with few drops of 10% saline water. The paste hardened within five minutes. The set cement had a surface pH near 5. The surface pH reached to near 7 within less than half hour after setting.

EXAMPLE 4

$CaNaPO_4$ pure ceramic was prepared by solid reaction at high temperatures. Required amounts of $(NH_4)_2 HPO_4$, $Na_2CO_3$ and $CaCO_3$ were mixed homogeneously and sintered. The sintered ceramic has the same x-ray pattern as those prepared from Example 1. The sintered solid was then ground to fine powder. 1.5 g of anhydrous citric acid and 1.5 g of trisodium citrate was dissolved in 5 ml of pure water to form the setting solution. 1 g of prepared $CaNaPO_4$ ceramic powder was mixed with 1 g of anhydrous calcium sulfate. This mixed powder was then mixed with a few drops of the setting solution to form a paste which set in a few minutes. The surface pH was near 6 at the beginning, and inceased to 7 or higher within a half hour after setting. No signs of surface disintegration were shown after soaking the set cement in pure water.

EXAMPLE 5

Mixed ceramics of $CaNaPO_4$ with the chemical composition of $1.2\ CaO.1.8\ Na_2O.P_2O_5$ were prepared by solid state reaction at high temperatures. Required amounts of $(NH_4)_2 HPO_4$, $CaCO_3$ and $Na_2CO_3$ corresponding to the above chemical composition were mixed homogeneously and sintered. The sintered ceramic was then ground to fine powder. This prepared ceramic has high alkalinity and dissolves much faster than other calcium ceramics. 2 g of the above prepared ceramic fine powder was mixed with 0.4 g of anhydrous citric acid and 0.4 g of trisodium citrate. This mixed powder was then mixed with few drops of pure water to form a paste. The surface pH of the set cement was near 7.

Examples 1–5 use calcium and sodium phosphate ceramics, but calcium potassium phosphate ceramics can be used interchangeably with the calcium sodium phosphate ceramics and, thus, also react with citric acid or acidic citrate salts to form biocompatible and resorbable cements. It should be understood that the foregoing disclosure emphasizes certain embodiments of the invention and that all modifications or alternatives thereto are within the spirit and scope of the invention.

I claim:

1. A surgical cement for orthopedic, dental, and maxillofacial applications comprising:
   a cementing powder selected from the group of calcium alkali phosphate ceramics consisting of calcium sodium phosphate or calcium potassium phosphate ceramics;
   a setting reagent selected from the group of acidic citrates consisting of citric acid or acidic citrate salts wherein the weight ratio of cementing powder to setting reagent lies between 1.2:1 and 10:1; and
   an effective amount of an aqueous setting solution selected from the group consisting of sterilized pure water and saline water to form a cementitious paste, said paste reaching a neutral pH of 7 shortly after setting.

2. The surgical cement of claim 1 wherein the cementing powder is selected from the group consisting of $CaNaPO_4$ or $Ca_5Na_2(PO_4)_4$.

3. The surgical cement of claim 1 wherein the cementing powder selected from the group of calcium alkali phosphate ceramics consists of mixed ceramics as a crystalline solution containing $Ca_3(PO_4)_2$, $CaNaPO_4$ and $Ca_5 Na_2 (PO_4)_4$, and has an overall chemical composition ranging from 2.9 CaO.0.1 $Na_2O.P_2O_5$ to 2.0 $CaO.Na_2O.P_2O_5$ prepared from solid state reaction at high temperatures.

4. The surgical cement of claim 1 wherein the calcium alkali phosphate ceramic further comprises mixed ceramics of $CaNaPO_4$ and $Na_3PO_4$ having an overall chemical composition ranging from 2.0 $CaO.Na_2O.P_2O_5$ to 0.8 $CaO.2.2 Na_2O.P_2O_5$ prepared from solid state reaction at high temperatures.

5. The surgical cement of claim 1 wherein the calcium alkali phosphate ceramic comprises $CaKPO_4$.

6. The surgical cement of claim 1 wherein the calcium alkali phosphate ceramic is a mixed ceramic as a crystalline solution of $Ca_3(PO_4)_2$ and $CaKPO_4$, and has an overall chemical composition ranging from 2.9 CaO.0.1 $K_2O.P_2O_5$ to 2.0 CaO.1.0 $K_2O.P_2O_5$ prepared from solid state reaction at high temperatures.

7. The surgical cement of claim 1 wherein the calcium alkali phosphate ceramic further comprises a mixed ceramic of $CaKPO_4$ and $K_3PO_4$ having an overall chemical composition ranging from 2.0 $CaO.K_2O.P_2O_5$ to 0.8 $CaO.2.2 K_2O.P_2O_5$ prepared from solid state reaction at high temperatures.

8. The surgical cement of claim 1 wherein the setting reagent selected from the group of acidic citrates comprises citric acid and at least one of the following citrate compounds: $NaH_2$ citrate, $Na_2H$citrate, $KH_2$ citrate, $K_2H$citrate, $NH_4H_2$ citrate, and $(NH_4)_2$ Hcitrate.

9. The surgical cement of claim 1 further including a soluble pH adjusting reagent.

10. The surgical cement of claim 9 wherein said soluble pH adjusting reagents are selected from the group consisting of: NaOH, KOH, $NH_4OH$, $Na_3$citrate, $K_3$citrate, $(NH_4)_3$ citrate, $Na_3PO_4$, $Na_2HPO_4$, $K_3PO_4$, or $K_2HPO_4$.

11. The surgical cement of claim 9 wherein said soluble pH adjusting reagent is premixed with said cementing powder and said setting reagent.

12. The surgical cement of claim 9 wherein said soluble pH adjusting reagent is dissolved in said aqueous setting solution.

13. The surgical cement of claim 1 wherein the cementing powder further comprises a filler up to approximately 5:1 by weight of said filler to cementing powder, wherein said filler is a powder of granule form having a particle size ranging from a few microns to 20 mesh.

14. The surgical cement of claim 13 wherein the filler is selected from the group consisting of tetracalcium phosphate, α-tricalcium phosphate, β-tricalcium phosphate, calcium phosphate apatite, octacalcium phosphate, dicalcium phosphate, calcium carbonate, calcium oxide, calcium hydroxide, calcium sulfate dihydrate, calcium sulfate hemihydrate, calcium anhydrous, calcium fluoride, calcium citrate, magnesium oxide, magnesium hydroxide, and collagen.

15. The surgical cement of claim 1 further comprising up to approximately 20% of an antibiotic.

16. The surgical cement of claim 1 further comprising up to approximately 10% bone growth protein.

17. A kit for making a surgical cement for orthopedic, dental, and maxillofacial applications comprising:
   a cementing powder consisting of calcium alkali phosphate ceramics; and
   a setting reagent selected from the group of acidic citrates consisting of citric acid or acidic citrate salts,
   said cementing powder and said setting reagent, when admixed with an effective amount of an aqueous solution forms a cementitious paste, which after setting, will attain a pH of at least 7.

* * * * *